(12) United States Patent
Stack et al.

(10) Patent No.: US 12,097,091 B1
(45) Date of Patent: Sep. 24, 2024

(54) OTO-BLOCK APPLICATOR AND METHOD

(71) Applicants: Justin Stack, Santa Cruz, CA (US); Seok Won Yoon, Fresh Meadows, NY (US); Giuseppe Massara, Vicenza (IT)

(72) Inventors: Justin Stack, Santa Cruz, CA (US); Seok Won Yoon, Fresh Meadows, NY (US); Giuseppe Massara, Vicenza (IT)

(73) Assignee: SPEK Research Inc., Santa Cruz, CA (US)

( * ) Notice: Subject to any disclaimer, the term of this patent is extended or adjusted under 35 U.S.C. 154(b) by 795 days.

(21) Appl. No.: 17/236,870

(22) Filed: Apr. 21, 2021

(51) Int. Cl.
  *B29C 33/38* (2006.01)
  *A61F 11/08* (2006.01)
  *A61M 31/00* (2006.01)

(52) U.S. Cl.
  CPC ........... *A61F 11/08* (2013.01); *A61M 31/007* (2013.01); *B29C 33/3857* (2013.01); *A61M 2210/0668* (2013.01)

(58) Field of Classification Search
  CPC ........... B29C 33/5857; H04R 2460/17; A61M 31/007; A61F 11/08
  USPC .................................. 128/864, 897; 381/329
  See application file for complete search history.

(56) References Cited

U.S. PATENT DOCUMENTS

| | | |
|---|---|---|
| 5,804,109 A | 9/1998 | Perkins |
| 8,465,685 B2 | 6/2013 | Öquist |
| 10,070,235 B2 | 9/2018 | Schwarzlos-Sooprayen et al. |
| 2009/0266369 A1* | 10/2009 | Johnson .................. A61F 11/08 128/864 |
| 2013/0223666 A1* | 8/2013 | Michel .................. H04R 25/00 381/329 |
| 2014/0254847 A1* | 9/2014 | Howard .................. H04R 25/00 381/329 |

* cited by examiner

*Primary Examiner* — Robert B Davis
(74) *Attorney, Agent, or Firm* — Plager Schack LLP; Mark H. Plager; Naomi Mann

(57) ABSTRACT

An oto-block applicator, includes a plunger, an oto-block holder configured to couple to the plunger; and an insertion stop coupled to said oto-block holder, wherein the insertion stop is configured to prevent insertion of the oto-block holder past a predetermined distance into the ear, and the plunger is configured to push an oto-block held within the oto-block holder out of a front end of the oto-block holder and into the user's ear.

8 Claims, 4 Drawing Sheets

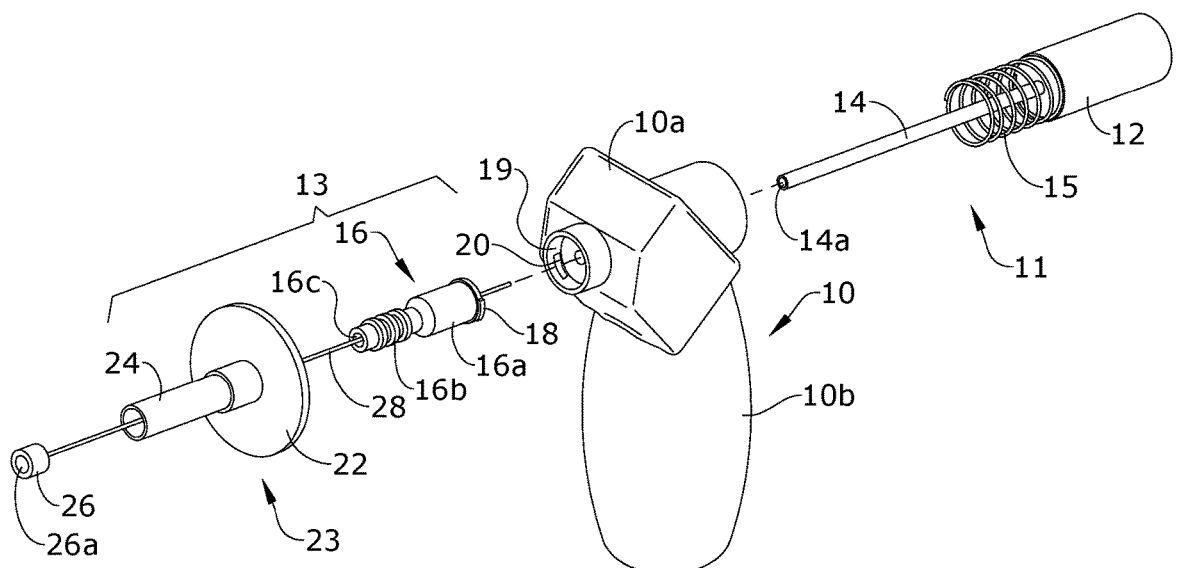
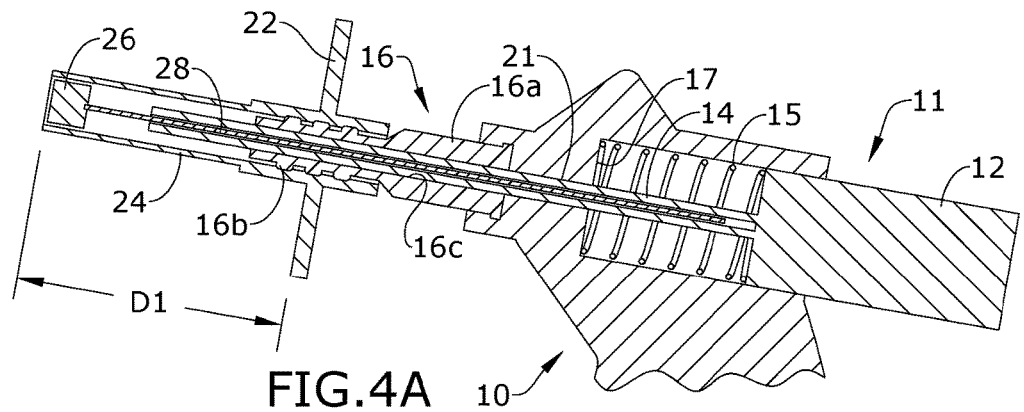
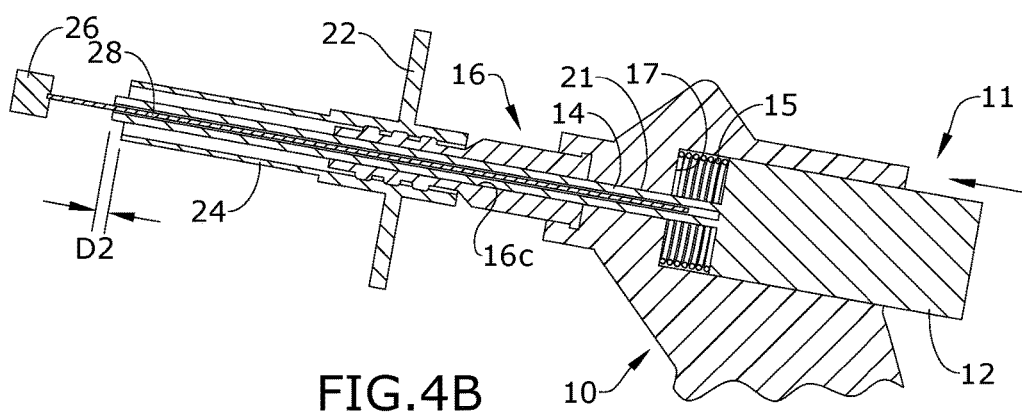

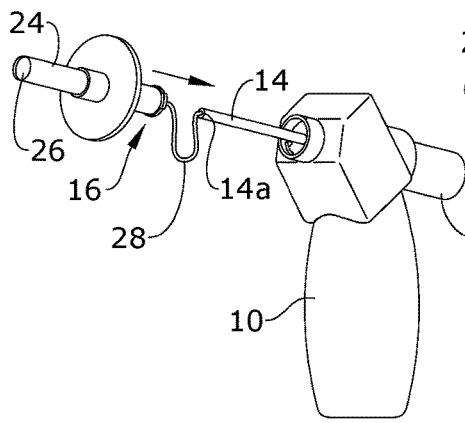
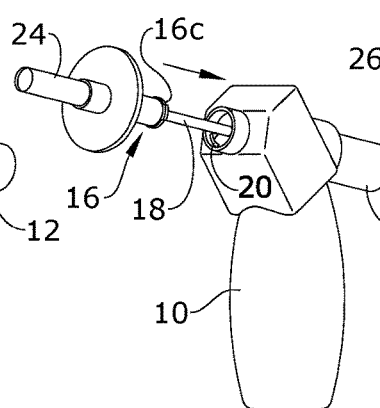
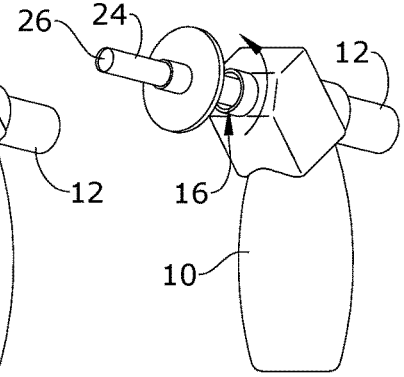
FIG.5A　　　　　FIG.5B　　　　　FIG.5C
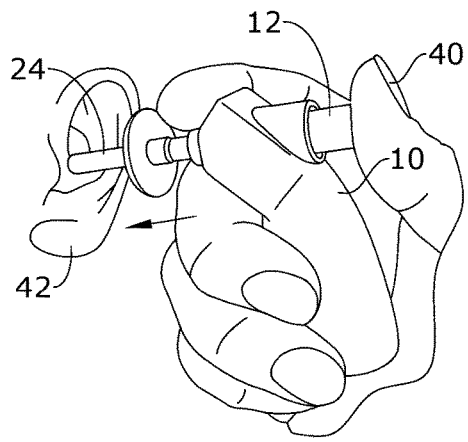
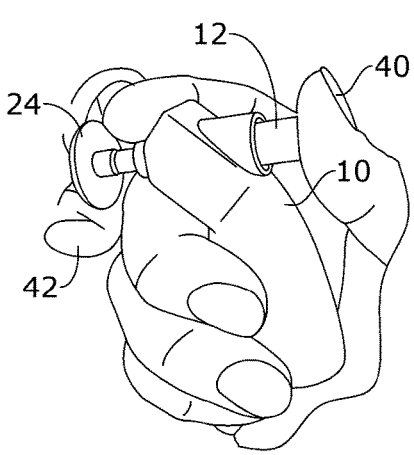
FIG.6A　　　　　FIG.6B
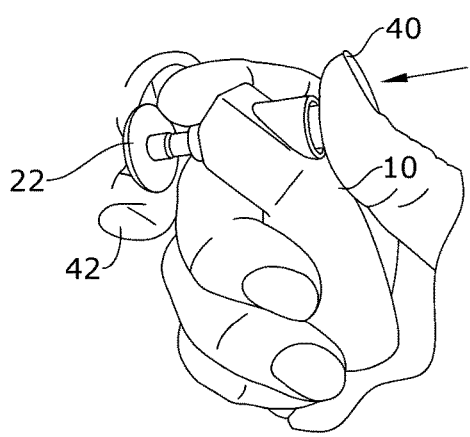
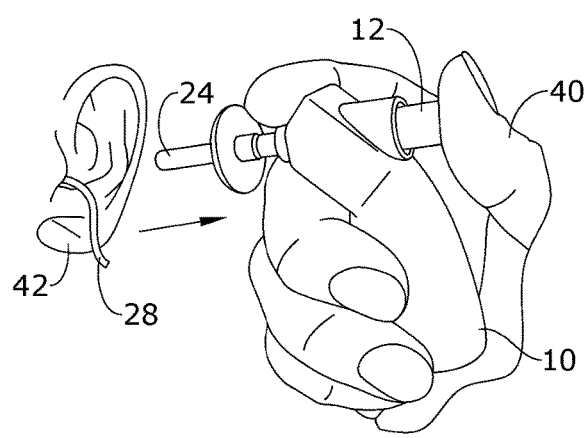
FIG.6C　　　　　FIG.6D

OTO-BLOCK APPLICATOR AND METHOD

BACKGROUND

The embodiments herein relate generally to devices and methods for making customized ear products, and more specifically to methods of creating an accurate impression of the ear canal using molded impressions.

Producing customized ear products requires obtaining an accurate impression of the ear canal. Due to the curvature of the ear, this may be challenging, particularly for the untrained consumer. Certain digital methods may employ cameras and/or scanning devices on consumer electronics for obtaining an ear canal impression. Such methods may be limited in the device's ability to 'see' far enough past the first bend of the ear canal to obtain accurate data.

Other methods may entail obtaining a mold impression of the ear by inserting or stuffing an impression material into the ear canal. This may typically involve first inserting an oto-block into the ear canal in order to protect the ear drum from the impression material. However, inserting the oto-block and hence the impression material deeply enough to obtain an accurate impression may be challenging as well.

As such, there is a need for an improved system for creating accurate ear impressions, and particularly for such systems which may be employed used by both professional and unprofessional users.

SUMMARY

According to various embodiments, disclosed is a system for creating an impression of an ear canal, comprising an applicator and an applicator method for safely inserting an oto-block into the ear canal. The disclosed system enables an untrained user to safely take an accurate ear impression that may reach past the first bend of the ear canal. As such, consumers may take ear impressions at home to use for ordering various products that require an ear mold through the mail or online.

In embodiments, the disclosed applicator has a stopper disc, and plunger release mechanism that is configured to insert the oto-block to a predetermined depth, and ensure it reaches a proper and safe distance into the ear canal, for creating a reliable custom ear product. Additionally, the disclosed system uses a vented oto-block which prevents pressure build up when stuffing the impression material.

BRIEF DESCRIPTION OF THE FIGURES

The detailed description of some embodiments of the invention is made below with reference to the accompanying figures, wherein like numerals represent corresponding parts of the figures.

FIG. 3 is an exploded view of the oto-block applicator;

FIG. 4A is a section view taken along line 4-4 in FIG. 1, wherein a spring element of the applicator is shown in a neutral position;

FIG. 4B is a section view similar to FIG. 4A, but illustrating the spring element in a compressed position, as it is pushed by a plunger of the applicator;

FIGS. 5A-C illustrate steps for assembling the applicator shown in FIG. 2, in accordance with certain embodiments;

FIG. 5A depicts a first step of assembling the applicator;

FIG. 5B depicts a second step of assembling the applicator;

FIG. 5C depicts a third step of assembling the applicator;

FIGS. 6A-D illustrate steps for inserting an oto-block into an ear canal using the assembled oto-block applicator according to certain embodiments;

FIG. 6A depicts a first step of inserting the oto-block;

FIG. 6B depicts a second step of inserting the oto-block;

FIG. 6C depicts a third step of inserting the oto-block;

FIG. 6D depicts a fourth step of inserting the oto-block;

FIG. 8A depicts a first step of forming an ear canal impression, comprising inserting the activated impression material depicted in FIG. 7B into the ear canal;

FIG. 8B depicts a second step of forming the ear canal impression, comprising inserting further impression material into the ear canal;

FIG. 8C depicts a third step of forming the impression, comprising agitating the inserted impression material and/or ear;

FIG. 8D depicts a forth step of forming the impression, comprising removing the impression material and oto-block from the ear canal, wherein the impression material has hardened to form the ear canal impression.

DETAILED DESCRIPTION OF CERTAIN EMBODIMENTS

Figure 1:
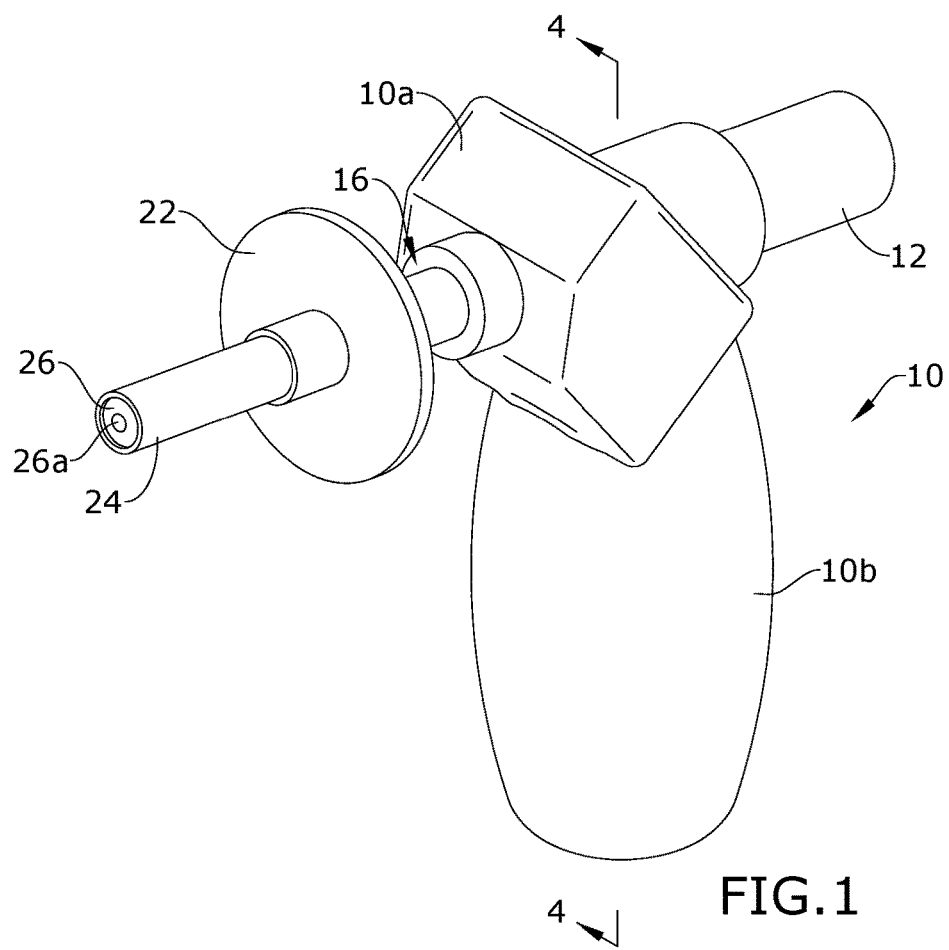
FIG. 1 is a perspective view of an oto-block applicator, which is in an assembled state, according to certain embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Creating an accurate impression of the ear canal may be a critical element in producing custom ear products such as ear molds, ear plugs, ear buds, ear phone IEM adapters, hearing aids, etc. The disclosed subject matter provides a system that enables either trained or untrained users to safely take an accurate impression of the ear canal. As such, the untrained user may create an impression at home for use in ordering various products through the mail or Internet, without having to visit a professional such as an audiologist.

According to certain embodiments as depicted in the figures, the disclosed system provides an oto-block applicator configured to safely insert an oto-block 26 into the canal of a human ear 42. In embodiments, oto-block 26 may have a cylindrical body made of a material such as foam, and may comprise a pull element 28 for enabling the oto-block to be pulled out of the ear canal. In further embodiments, oto-block 26 may be vented for preventing pressure build up, i.e. permitting pressure release, when stuffing the impression material into the ear canal. In some embodiments, pull element 28 may be a vent tube which may provide the oto-block with its venting functionality (as well as enabling it to be pulled out of the ear). Pull element 28 ("vented pull element 28") may comprise for example, a flexible silicone vent tube that acts similar to a thread (such as used in standard oto-blocks), and may be attached through the center 26a of the oto-block. It should be appreciated that the disclosed subject matter may be used with various types of oto-blocks, including non-vented oto-blocks, which may comprise a standard non-vented thread (e.g. cotton thread or the like).

In certain embodiments as best depicted in FIGS. 1-5C, the oto-block applicator may comprise an applicator body 10, a plunger 11, and oto-block holder 13. Applicator body 10 may include a top portion 10a configured to retain plunger 11 and oto-block holder 13, and a bottom portion 10b which may serve as a handle for the applicator. In certain embodiments, top portion 10a of applicator body 10 may comprise a plunger cavity 10c within a back side of top portion 10a. The plunger cavity may be configured to slidably receive and/or retain plunger 11.

Plunger 11 may be configured to push oto-block 26 out of oto-block holder 13. In embodiments, plunger 11 may comprise a plunger stem 14 coupled to a plunger base 12 as best depicted in FIGS. 3-4B. In some embodiments, plunger stem 14 may include a stem aperture 14a configured to permit vented pull element 28 to pass therethrough. In some embodiments, the plunger may be pre-assembled with applicator body 12. As depicted in the figures, cavity 10c/plunger base 12 may comprise corresponding tubular/cylindrical configurations according to certain embodiments. It should be appreciated however, that other geometric shapes may be employed without departing from the inventive concept.

As best depicted in FIGS. 4A and B, a spring 15 may be positioned between a front wall 17 of cavity 10c and plunger base 12 to provide push back tension on plunger 11. As such, the spring is configured to push the plunger back to its original position, enabling its reuse; and may further assist in helping a user control the release speed of the oto-block. It should be appreciated that an alternate elastic element, such as a band, may replace the spring according to various embodiments.

In certain embodiments, top portion 10a of applicator body 10 may further comprise an applicator connector 19 configured to connect oto-block holder 13 to applicator body 10. In embodiments, applicator connector 19 may generally be positioned opposite plunger cavity 10c, on a front side of top portion 10a. Additionally, an applicator aperture 21 may run through connector 19 to plunger cavity 10c, for permitting plunger stem 14 to pass therethrough.

Figure 2:
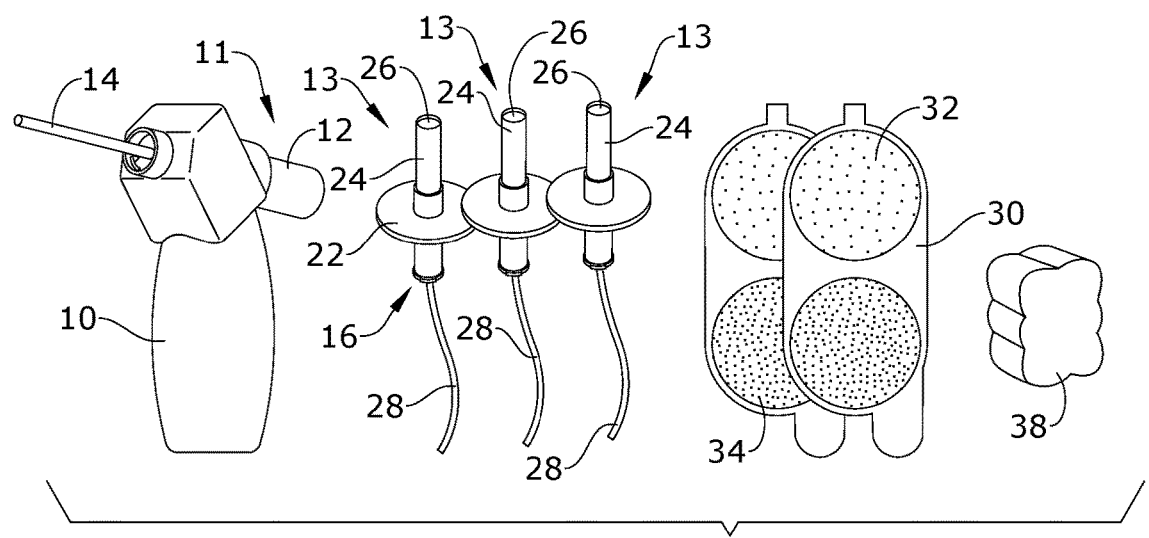
FIG. 2 is a schematic view of an impression taking kit including the oto-block applicator in a disassembled state, according to certain embodiments.
Figure 7A:
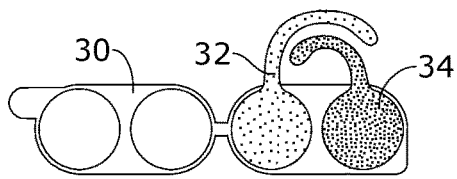
FIG. 7A depicts first and second impression premix components of the impression taking kit of FIG. 2, which are used to form an activated impression material.
Figure 7B:
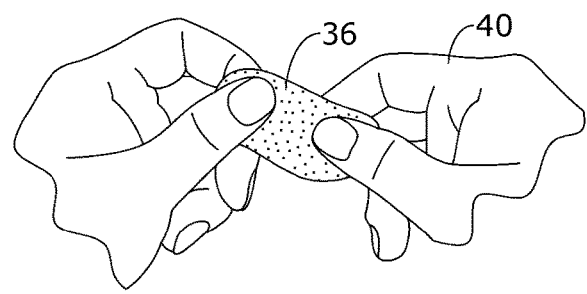
FIG. 7B depicts a step of kneading or mixing the first and second premix components depicted in FIG. 7A, to form the activated impression material ready for use.

In certain embodiments as best depicted in FIG. 2, oto-block holder 13 may comprise a nozzle fitting 16 and an applicator tip 23. Nozzle fitting 16 may comprise a back portion 16a configured to connect to applicator connector 19. Nozzle fitting 16 may further comprise a front portion 16b configured to connect or bond to applicator tip 23. Additionally, nozzle fitting 16 may include a fitting aperture 16c, permitting plunger stem 14 to pass therethrough. In embodiments, applicator tip 23 may have a tubular configuration and may be jacketed over front portion 16b of the nozzle fitting. According to various embodiments, nozzle fitting 16 and applicator tip 23 may be permanently attached. According to an exemplary embodiment, nozzle fitting 16 may be formed from a hard material, such as plastic, and the like, while applicator tip 23 may be formed from a flexible/stretchy material, such as silicone, rubber, foam, etc. Additionally, nozzle fitting 16 may comprise rings or barbs, as shown, wherein applicator tip 23 may be stretched or pressure fit over nozzle fitting 16. In some other embodiments, an adhesive may be used to bond the components together. It should be appreciated that various materials, geometric configurations, attachment mechanisms etc., may be employed without departing from the inventive concept.

In embodiments, back portion 16a of nozzle fitting 16 is configured to lockably engage and disengage from connector 19. For example, as depicted in the figures, the back portion of nozzle fitting 16 may be cylindrically shaped and include a locking tab 18 while connector 19 may include a cylindrical hollow comprising a locking tab receiver 20, whereupon nozzle fitting 16 may be inserted into connector 19 and twisted in a first direction to lockably engage the locking tab 18 within tab receiver 20. Twisting nozzle fitting in a second direction, opposite the first, may thereafter disengage the components. It should be appreciated that other mechanisms for fastening nozzle fitting 16 to connector 19 may be employed, e.g. a threaded connection, without departing from the inventive concept.

In certain embodiments, applicator tip 23 may comprise a tip nozzle 24, configured to hold oto-block 26, wherein oto-block 26 may be pushed out of the front end of the tip nozzle 24 (or front end of the oto-block holder) via plunger stem 14 (see FIG. 4B). As shown in the figures, and in accordance with an exemplary embodiment, tip nozzle 24 may be a stretchy and/or flexible tubular member having an internal diameter conforming to the external diameter of oto-block 26, to provide a snug and/or compressed hold of the oto-block. The plunger stem 14 may then break that hold when pushed against the oto-block, releasing it from the tip nozzle 24.

Applicator tip 23 may further comprise an insertion stop element 22 (or flange 22) configured to guide insertion of the oto-block to a proper and safe distance. Flange 22 may be shaped, for example, as a disc as shown in the figures; however other geometric shapes may be employed.

In its assembled state as best depicted in FIGS. 1, 4A and B, and 5C, at least a portion of plunger base 12 may slidably reside within plunger cavity 10c, and oto-block holder 13 may be connected to applicator connector 19 of applicator body 10. Plunger stem 14 may extend through apertures 21 and 16c, which may be centrally aligned, and oto-block 26 may be held within tip nozzle 24 of oto-block holder 13. Vented pull element 28 may further pass-through stem aperture 14a. In this state, plunger 11 may be used to push the oto-block out of the holder by pushing plunger base 12 forward, whereby oto-block 26 is pushed forward by plunger stem 14 to release it into the ear canal.

According to an exemplary embodiment, to keep the applicator at a safe distance for insertion of the oto-block, and/or to prevent the oto-block from inserting too deeply into the canal, flange 22 may be positioned at a distance 'd1' of approximately 25 mm from the end of tip nozzle 24 (see FIG. 4A). Additionally plunger stem 14 may extend a distance 'd2' of approximately 1 mm from the tip nozzle 24 in the fully forward/fully compressed state of the spring (see FIG. 4B).

According to certain embodiments as best depicted in FIGS. 5A-9, once the oto-block applicator is assembled and loaded with the oto-block, it may be used to insert the oto-block into an ear canal. After insertion of the oto-block, impression material may be stuffed into the ear and allowed to harden in order to form the ear canal impression.

According to an exemplary embodiment, a user may be provided with an impression taking kit as depicted in FIG. 2, which may comprise a plurality of oto-block holders 26, which may each contain a pre-inserted oto-block 26. The kit may further comprise an applicator body 10, which may be pre-assembled with plunger 11. The kit may also include impression material 30, which may be provided in a quantity sufficient to create multiple impressions. In embodiments, the impression material 30 may comprise a first premix component 32 and a second premix component 34, which may be mixed to create an activated impression material 36 that is ready for use. The impression material may be, for example, a silicone-based material such as Otoform™, wherein first and second premix components 32, 34, may be pastes, that when mixed together, form activated impression material 36 which is a putty that is catalyzed for hardening.

In embodiments, the impression taking kit may be used for creating an ear canal impression by first attaching oto-block holder 13 to the applicator body 10 as depicted in FIGS. 5A-C. This process may comprise inserting vented pull element 28 into stem aperture 14a of plunger stem 14 (see FIG. 5A). Nozzle fitting 16 may then be slid over plunger stem 14, to insert stem 14 into fitting aperture 16c (see FIG. 5B). Nozzle fitting 16 may thereafter be inserted and locked to applicator connector 19 by twisting locking tab 18 of the nozzle fitting into locking tab receiver 20 of applicator body 10 (see FIG. 5C).

Once assembled, the applicator may be used to insert the oto-block into the ear canal, as depicted in FIGS. 6A-D. This process may comprise first inserting the tip nozzle 24 containing oto-block 26 into the ear canal, as depicted in FIGS. 6A and B. In embodiments, this should be performed slowly, wherein the user may swivel the applicator to find the right insertion angle. Once the proper insertion angle is determined, the tip nozzle 24 may be further inserted until flange 22 contacts the outer ear (see FIG. 6B). The user may then press against plunger base 12, whereby plunger stem 14 pushes against the oto-block to release it into the ear canal, wherein vented pull element 28 may dangle out of the ear (see FIGS. 6C and D). In embodiments, the user may need to slowly push the plunger base 12 several times to release the oto-block from the applicator. Thereafter, the user may slowly remove applicator from the ear, being careful not to pull vented pull element 28 while doing so. As shown in the figures, the bottom portion 10b of applicator body 10 provides a handle which enables the user to comfortably hold the applicator in his/her hand 40, while using the thumb to press against the plunger base. Additionally, spring 15 forces the plunger base to its original position, enabling its reuse. The push back tension of the spring may further assist a user in controlling the release speed of the oto-block as it is inserted.

Once the oto-block 26 is inserted into the ear canal, the user may insert the impression material into the ear to form a hardened ear canal impression, as depicted in FIGS. 7A-9. This process may comprise first mixing or kneading the first premix component 32 with the second premix component 34 to form the activated impression material 36 (see FIGS. 7A and B). In embodiments, the premix components may be provided in different colors, wherein sufficient mixing may be indicated color uniformity of the resultant mixture. According to various embodiments, the kneading process may take about 10-20 seconds, or about 15 seconds or less. Additionally, as hardening of the activated impression material initiates upon mixing, the premix components should be kneaded immediately prior to inserting the material into the ear canal.

Figure 8A:
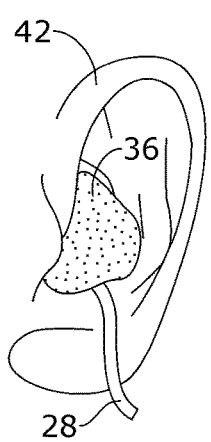
FIGS. 8A-D illustrate steps for forming an ear canal impression using the activated impression material depicted in FIG. 7B, wherein the oto-block has been pre-inserted into the ear canal.
Figure 8B:
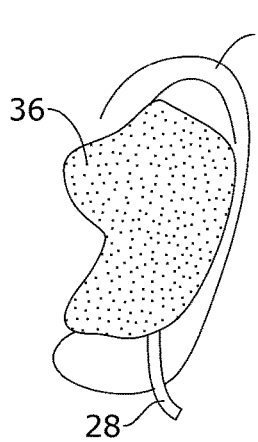
Figure 8C:
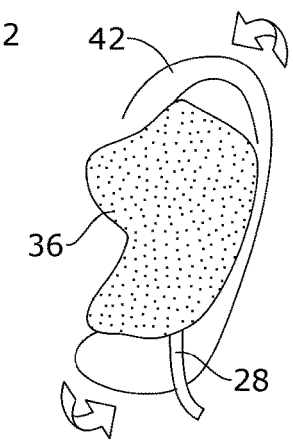
Figure 8D:
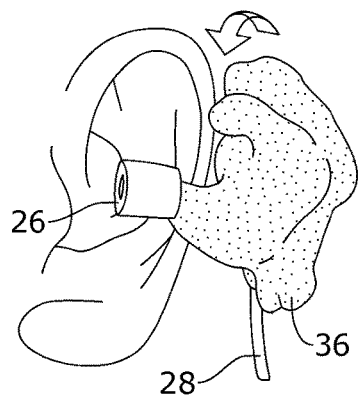
Figure 9:
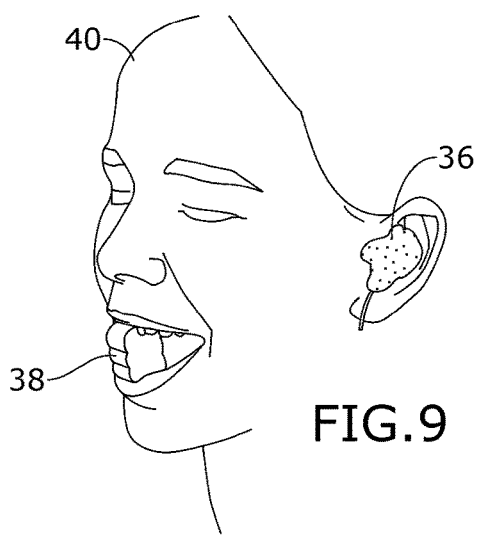
FIG. 9 depicts the use of a bite block while forming the ear canal impression.

Once the components have been sufficiently mixed, the user may begin inserting or hand-stuffing the resultant impression material 36 into the ear canal as depicted in FIGS. 8A-D. This may comprise first stuffing impression material 36 into the inner most depth (i.e. against the oto-block), and working out from there (see FIGS. 8A and B). Stuffing of the impression material may be performed in a kneading fashion and with light to medium pressure to ensure filling of all the spaces and crevasses of the ear canal. In embodiments, the oto-block vent tube 26a may help release pressure built up in the ear canal when the impression material is stuffed. This permits impression material to be properly stuffed and/or inserted to a sufficient depth. Once the ear is fully stuffed, the impression material is allowed to cure or harden. In embodiments, hardening may take about 5 to 10 minutes, or about 7 minutes, depending on factors such as type and/or condition of the impression material, user speed, ambient conditions, etc. In some embodiments, the user may press his/her finger against the impression material to determine proper curing. In some embodiments, a bite block 38 may be used while forming the impression, as shown in FIG. 9. Once the impression material has fully hardened, the user may remove the formed impression from the ear, with the oto-block from the ear, as shown in FIG. 8D. In some embodiments, the user may massage the ear love in a circular motion (see FIG. 8C) to loosen the material prior to removal.

The constituent elements of the disclosed device and system listed herein are intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device. Terms such as 'approximate,' 'approximately,' 'about,' etc., as used herein indicate a deviation of within +/−10%. Relationships between the various elements of the disclosed device as described herein are presented as illustrative examples only, and not intended to limit the scope or nature of the relationships between the various elements. Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. An oto-block applicator, comprising:
   a plunger;
   an oto-block holder configured to couple to said plunger; and
   an insertion stop coupled to said oto-block holder,
   wherein at least a portion of the oto-block holder is configured to insert into a user's ear,
   wherein the insertion stop is configured to prevent insertion of the oto-block holder past a predetermined distance into the ear,
   wherein movement of the plunger towards the oto-block holder is configured to push an oto-block held within the oto-block holder out of a front end of the oto-block holder and into the user's ear, when the oto-block holder is inserted into the user's ear,
   wherein the oto-block holder comprises a tubular member including a front end that defines said front end of the oto-block holder, the tubular member being configured to releasably hold said oto-block inserted therein,
   wherein the plunger comprises a plunger stem that extends into the tubular member when the oto-block holder is coupled to the plunger, the plunger stem further being movable towards the front end of the oto-block holder, wherein movement of the plunger stem towards said front end is configured to contact said oto-block held within the tubular member, and to push the oto-block out of the tubular member and into the user's ear when the oto-block holder is inserted into the user's ear, wherein said applicator further comprises a central applicator body, wherein the plunger is coupled to a back side of the central applicator body, wherein a back end the oto-block holder is configured to attach to a front side of the central applicator body, opposite the plunger, wherein the central applicator body includes a bottom portion forming a handle of the oto-block applicator, and wherein the plunger is coupled to a top portion of the central applicator body above the handle.

2. The oto-block applicator of claim 1, further comprising an elastic element configured to impose resistance against movement of the plunger towards the oto-block holder.

3. The oto-block applicator of claim 1, wherein the central applicator body comprises a connector configured to lockably engage the oto-block holder, the connector located at the top portion of the applicator body and opposite the plunger.

4. The oto-block applicator of claim 3, wherein said central applicator body comprises a plunger cavity configured to slidably retain the plunger.

5. The oto-block applicator of claim 4, the plunger further comprising a plunger base coupled to said plunger stem, the oto-block applicator further comprising a spring within the plunger cavity, the spring being positioned between a front wall of the plunger cavity and the plunger base, wherein the spring is configured to impose push back tension on the plunger.

6. An oto-block insertion system, comprising:
an oto-block; and
an oto-block applicator including:
a plunger;
an oto-block holder configured to hold said oto-block and to couple to said plunger; and
an insertion stop coupled to said oto-block holder;
wherein at least a portion of the oto-block holder is configured to insert into a user's ear,
wherein the insertion stop is configured to prevent insertion of the oto-block holder past a predetermined distance into the ear,
wherein movement of the plunger towards the oto-block holder is configured to push the oto-block out of a front end of the oto-block holder and into the user's ear, when the oto-block is held within the oto-block holder and the oto-block holder is inserted into the user's ear, and wherein the oto-block is a vented oto-block.

7. The oto-block insertion system of claim 6, wherein the oto-block holder comprises a tubular member including a front end that defines said front end of the oto-block holder, the tubular member being configured to releasably hold an oto-block inserted therein, wherein the plunger comprises a plunger stem that extends into the tubular member when the oto-block holder is coupled to the plunger, the plunger stem being movable towards the front end of the oto-block holder, wherein the oto-block comprises a vented pull element attached to an oto-block body, wherein the plunger stem includes an aperture that is configured to receive said vented pull element therein, wherein movement of the plunger stem towards said front end is configured to contact the oto-block when the oto-block is held within the tubular member, and to push the oto-block out of the tubular member and into the user's ear when the oto-block holder is inserted into the user's ear.

8. The oto-block insertion system of claim 6, wherein said oto-block applicator further comprises a central applicator body, wherein the plunger is coupled to a back side of the central applicator body, and wherein a back end the oto-block holder is configured to attach to a front side of the central applicator body, opposite the plunger.

\* \* \* \* \*